(12) United States Patent
Tao

(10) Patent No.: US 11,257,241 B2
(45) Date of Patent: *Feb. 22, 2022

(54) SYSTEM AND METHOD FOR COMPONENT POSITIONING BY REGISTERING A 3D PATIENT MODEL TO AN INTRA-OPERATIVE IMAGE

(71) Applicant: Radlink, Inc., El Segundo, CA (US)

(72) Inventor: Wenchao Tao, Los Angeles, CA (US)

(*) Notice: Subject to any disclaimer, the term of this patent is extended or adjusted under 35 U.S.C. 154(b) by 371 days.

This patent is subject to a terminal disclaimer.

(21) Appl. No.: 16/212,065

(22) Filed: Dec. 6, 2018

(65) Prior Publication Data

US 2019/0180466 A1 Jun. 13, 2019

Related U.S. Application Data

(60) Provisional application No. 62/595,670, filed on Dec. 7, 2017.

(51) Int. Cl.
*G06K 9/00* (2006.01)
*G06T 7/70* (2017.01)
(Continued)

(52) U.S. Cl.
CPC .................. *G06T 7/70* (2017.01); *G06T 7/11* (2017.01); *G06T 7/13* (2017.01); *G06T 7/149* (2017.01); *G06T 7/187* (2017.01); *G06T 11/003* (2013.01); *G06T 17/00* (2013.01); *G06T 19/20* (2013.01); *A61B 2034/105* (2016.02);
(Continued)

(58) Field of Classification Search
CPC ... G06T 7/70; G06T 7/187; G06T 7/11; G06T 7/13; G06T 7/149; G06T 11/003; G06T 17/00; G06T 19/20; G06T 2207/10081; G06T 2207/10088; G06T 2207/10124; G06T 2207/20116; G06T 2207/20152; G06T 2207/30008; G06T 2210/41; G06T 2219/2016; A61B 2034/105

See application file for complete search history.

(56) References Cited

U.S. PATENT DOCUMENTS

| | | | | |
|---|---|---|---|---|
| 2015/0088145 | A1* | 3/2015 | McCarthy | A61B 34/10 606/91 |
| 2016/0100909 | A1* | 4/2016 | Wollowick | G06T 7/33 600/424 |
| 2018/0005411 | A1* | 1/2018 | Mu | G06T 11/003 |

* cited by examiner

*Primary Examiner* — Atiba O Fitzpatrick
(74) *Attorney, Agent, or Firm* — Cislo & Thomas, LLP; Kelly W. Cunningham

(57) ABSTRACT

Disclosed herein are a system and method that may help place or position a component, such as an acetabular cup or a femoral component, during surgery. An example system may iteratively register a plurality of two-dimensional projections from a three-dimensional model of a portion of a patient, the three-dimensional model being generated from a data set of imaging information obtained at a neutral position. An example system may further score each two-dimensional projection against an intra-operative image by calculating a spatial difference between corresponding points. A two-dimensional projection having a minimum score reflecting the smallest distance between the corresponding points may be identified. Using the two-dimensional projection having the minimum score, an adjustment score reflecting a difference in the values representing the orientation of the three-dimensional model at the intra-operative projection position and values representing the orientation of the three-dimensional model at the neutral position may be calculated.

21 Claims, 8 Drawing Sheets

(51) Int. Cl.
    *G06T 11/00*         (2006.01)
    *G06T 17/00*         (2006.01)
    *G06T 7/13*           (2017.01)
    *G06T 7/11*           (2017.01)
    *G06T 7/149*         (2017.01)
    *G06T 7/187*         (2017.01)
    *G06T 19/20*         (2011.01)
    *A61B 34/10*         (2016.01)

(52) U.S. Cl.
    CPC ............... *G06T 2207/10081* (2013.01); *G06T 2207/10088* (2013.01); *G06T 2207/10124* (2013.01); *G06T 2207/20116* (2013.01); *G06T 2207/20152* (2013.01); *G06T 2207/30008* (2013.01); *G06T 2210/41* (2013.01); *G06T 2219/2016* (2013.01)

SYSTEM AND METHOD FOR COMPONENT POSITIONING BY REGISTERING A 3D PATIENT MODEL TO AN INTRA-OPERATIVE IMAGE

TECHNICAL FIELD

This disclosure relates to a system and method for obtaining a proper placement and positioning of a component such as an acetabular cup or a femoral component during a surgical procedure.

BACKGROUND

Patients are often exposed to a series of x-ray radiation exposures during certain types of surgery, including during total hip arthroplasty and other orthopaedic procedures, because the patient may have to be placed in a desired position or orientation, moved around, and returned to the initial desired position during surgery. Furthermore, x-rays may be needed or desired to ensure proper placement of surgical components in the patient during surgery. Repeated x-rays may be taken to assure that, after the patient is moved, any components are in an optimal position and/or that the patient is returned to the desired position to complete surgery.

X-rays may also be used to determine one or more target positioning values for a component before a surgery. While such pre-operative x-ray images may provide a surgeon with a general idea of the patient's anatomy and approximate positioning values for a component, differences in the patient placement and/or x-ray device placement relative to each other when x-ray images are produced at different times may introduce variations to x-ray images. These variations may, for example, hinder a surgeon from determining exact, proper positioning values for a component during a surgery while looking at an intra-operative x-ray image. It may take multiple x-rays to precisely establish a patient at the neutral position.

Similarly, post-operation x-rays may be taken to confirm proper placement of any components, implants, prostheses, etc. For the same reasons, it is important that the patient position be consistent with the pre-operation and intra-operation patient position to ensure consistent measurements.

At the same time, however, it may be undesirable, difficult, or impossible to return a patient to a neutral position, especially during a surgery or immediately after a surgery.

In many surgeries, consistent and accurate component placement may be critical. In total hip arthroplasty, for example, accurate placement of an acetabular cup may allow the acetabular cup to have a long life with little wear. Deviations in positioning values of an acetabular cup, including inclination, anteversion, and/or tilt may contribute to a reduced life of the acetabular cup, increase the risk of post-operative dislocation, and the like.

It is accordingly desirable to confirm placement of a component during surgery, where the surgeon may make any beneficial adjustments to the prosthesis while the patient is still opened up. The inability of many medical professionals to reproduce exact pre-operative x-ray conditions intra-operatively may presently limit the utility of intra-operative x-rays to confirm an accurate component placement, thus increasing the risk that the component is inaccurately placed and increasing the risk of associated negative outcomes for the patient. Similarly, it may be desired to minimize patient movement during surgery, especially if the movement is solely for the purpose of obtaining x-ray images.

There is a need for a surgical system and associated techniques that improve the accuracy and reproducibility of determining and confirming proper positioning values of a component while limiting the exposure of a patient to x-ray radiation. There is an additional need for a surgical system and associated techniques that allow x-ray images yielding accurate measurements to be taken while reducing or eliminating the need to place the patient in the neutral position.

SUMMARY

The present disclosure provides a system and method that may be useful to determine a proper placement of a component during a surgery, such as the proper placement of an acetabular cup during total hip arthroplasty. Similarly, the system and method of the present disclosure may be useful to measure a component position and accurately adjust the component if needed to achieve a target component placement. Before surgery, a surgeon or other medical personnel may obtain image data of a patient, such as three-dimensional ("3D") image information of a patient or a portion of a patient. 3D imaging information may be obtained using computed tomography ("CT"), magnetic resonance imaging ("MRI") or nuclear magnetic resonance imaging ("NMR"), and the like. Modern 3D imaging techniques and systems may be precise. 3D imaging techniques may produce volumetric data, or a 3D data set comprising series of 2D slices taken at regular intervals. Using the 3D data set of imaging information, a 3D model of the imaged patient or imaged portion of the patient may be obtained. From the 3D model, one or more two-dimensional ("2D") projections of the 3D model may be obtained. A 2D projection may simulate a more traditional radiographic image, such as an x-ray image.

As used herein, a "neutral position" refers to the position of the patient being imaged (or a portion of the patient being imaged) before substantively commencing surgery, often pre-operatively. Imaging information taken at a neutral position may be used as a reference point against which to compare later imaging information, such as intra-operative or post-operative imaging information. If spatial values are assigned to imaging information, imaging information (or one or more portions thereof) obtained at a neutral position may be defined as an origin.

An aspect of the present disclosure is directed to a method of positioning a component intra-operatively that includes the steps of iteratively registering a plurality of two-dimensional projections of a portion of a patient from a three-dimensional model of the portion of the patient, the three-dimensional model being generated from a data set of imaging information obtained at a neutral position, and each two-dimensional projection having a spatial orientation; scoring each two-dimensional projection against an intra-operative image by determining a best fit of each projection to the intra-operative image and calculating a spatial difference between corresponding points; identifying a global minimum score reflecting the smallest spatial difference between the corresponding points on the two-dimensional projection and the intra-operative image and selecting the two-dimensional projection having the global minimum score as an intra-operative projection; obtaining values representing the orientation of the three-dimensional model corresponding to the intra-operative projection; and calculating an adjustment factor based on the difference in the values representing the orientation of the three-dimensional model at the intra-operative projection position and values representing the orientation of the three-dimensional model at the neutral position.

An alternate aspect of the present disclosure is directed to a method for positioning a component intra-operatively including the steps of receiving a data set of imaging information representing at least a first portion of a patient in a neutral position; generating a three-dimensional model of the first portion of the patient based on the data set of imaging information; receiving intra-operative imaging information representing the first portion of the patient; identifying a bony edge contour in the intra-operative imaging information; iteratively rendering a plurality of two-dimensional projections from the three-dimensional model, each two-dimensional projection having a corresponding spatial orientation; scoring each two-dimensional projection by calculating the distance of the bony edge contour in the intra-operative imaging information to a corresponding contour in each two-dimensional projection and identifying a global minimum score; outputting a transformation matrix for the two-dimensional projection having the global minimum score, the transformation matrix representing the orientation of the three-dimensional model relative to the neutral position when the two-dimensional projection having the global minimum score was rendered; and calculating an adjustment factor based on the transformation matrix.

In an embodiment, an example method may include a step of outputting a visual indication of an intra-operative adjustment to be made to a component based on the adjustment factor to achieve a target component orientation. Alternatively, an example method may include a step of applying the adjustment factor to an intra-operative leg length measurement and outputting a visual indication of an intra-operative adjustment to be made to the patient to achieve a target leg length measurement. Alternatively or additionally, a component may be an acetabular cup, a femoral component, measurement device or aid, or another type of orthopaedic implant or prosthesis.

In an embodiment, an example method may include a step of scoring a first two-dimensional projection occurs before or during the step of registering a subsequent two-dimensional projection. Alternately, an example method may include registering each of the plurality of two-dimensional projections before scoring any two-dimensional projection.

In an embodiment, the data set of imaging information may be the result of a three-dimensional imaging procedure such as CT or MRI. In an additional embodiment, the data set of imaging information may include volumetric imaging data. Further, in another embodiment, the three-dimensional model of the patient or the portion of the patient imaged may be generated by applying a region grow algorithm, a watershed algorithm, an active contour algorithm, or a combination thereof to the data set of imaging information.

Another aspect of the present disclosure is directed to an imaging system for intra-operatively positioning a component, the system including a computerized display system including a display, a receiver, and a microcontroller operatively coupled to the display and to the receiver and having access to system memory, the system memory including software instruction causing the microcontroller to perform the steps of: receiving a data set of imaging information representing at least a first portion of a patient in a neutral position; generating a three-dimensional model of the first portion of the patient based on the data set of imaging information; receiving intra-operative imaging information representing the first portion of the patient; identifying a bony edge contour in the intra-operative imaging information; iteratively rendering a plurality of two-dimensional projections from the three-dimensional model, each two-dimensional projection having a corresponding spatial orientation; scoring each two-dimensional projection by calculating the distance of the bony edge contour in the intra-operative imaging information to a corresponding contour in each two-dimensional projection and identifying a global minimum score; outputting a transformation matrix for the two-dimensional projection having the global minimum score, the transformation matrix representing the orientation of the three-dimensional model relative to the neutral position when the two-dimensional projection having the global minimum score was rendered; calculating an adjustment factor based on the transformation matrix; and outputting to the display a visual indication of an intra-operative adjustment to be made to a component based on the adjustment factor to achieve a target component orientation. In an embodiment of the system, a component may be an acetabular cup, a femoral component, measurement device or aid, or another type of orthopaedic implant or prosthesis. In a specific embodiment of the system, the component may be an acetabular cup; and the visual indication may include an outline of the target component orientation; real-time inclination, anteversion, and tilt values of the component; target inclination, anteversion, and tilt values of the component; and/or combinations thereof.

BRIEF DESCRIPTION OF THE DRAWINGS

The foregoing and other features of the present disclosure will become more fully apparent from the following description and appended claims, taken in conjunction with the accompanying drawings. Understanding that these drawings depict several examples in accordance with the disclosure and are, therefore, not to be considered limiting of its scope, the disclosure is described with additional specificity and detail below through the use of the accompanying drawings.

In the drawings.

DETAILED DESCRIPTION

Figure 1:
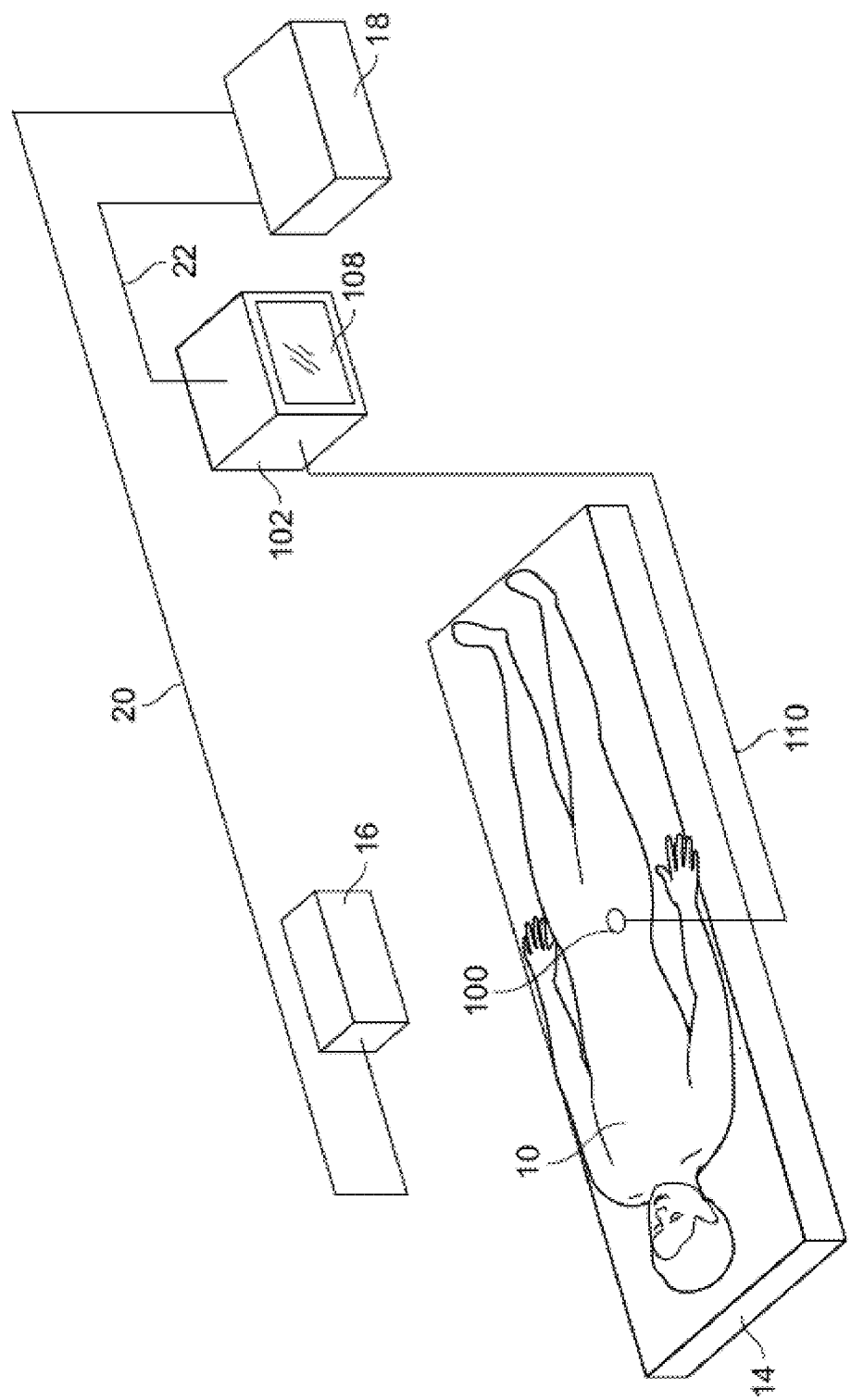
FIG. 1 is a block diagram view of an exemplary system and an associated patient and x-ray shows an embodiment of exemplary system architecture in accordance with an embodiment of the present disclosure.

In the following detailed description, reference is made to the accompanying drawings, which form a part hereof. In the drawings, similar symbols identify similar components, unless context dictates otherwise. The illustrative examples described in the detailed description and drawings are not meant to be limiting and are for explanatory purposes. Other examples may be utilized, and other changes may be made, without departing from the spirit or scope of the subject matter presented herein. It will be readily understood that the aspects of the present disclosure, as generally described herein and illustrated in the drawings, may be arranged, substituted, combined, and designed in a wide variety of different configurations, each of which are explicitly contemplated and make part of this disclosure.

Referring to FIG. 1, a computerized surgery assist computer 102 may receive anatomic image information of a patient 10 or a portion of a patient 10 (e.g., a pelvis) taken by an anatomical scanning device, such as an x-ray scanner 16 (e.g., when receiving discrete images or fluorographic images) at a position of the patient 10 (lying on a patient table 14). Alternatively, the computerized surgery assist computer 102 may receive anatomic image information of a patient 10 or a portion of a patient 10 obtained from a CT or MR scan. For example, in such an embodiment, the anatomic image information may be a data set of three-dimensional imaging information. In an embodiment, the computerized surgery assist computer 102 may receive a data set of three-dimensional imaging information obtained while the patient 10 was in a neutral position. The anatomic image information may be received from an image processing computer server 18 positioned via wired or wireless data links 20, 22 between the x-ray scanner 16 (or, e.g., the CT or MR scanner) and the surgery assist computer 102. Optionally, the patient may have a three-dimensional positional sensor 100 affixed to the patient's body, and the surgery assist computer 102 may receive positional information via wired or wireless data link 110 from sensor 100. The surgery assist computer 102 may be programmed to display a visual representation of the anatomic image information on a computerized display 108; determine a target positioning value of a component from the anatomic image information, either automatically or with input from a surgeon; and may make additional measurements as desired or programmed (e.g., measurements of one or more anatomical landmarks and/or ratios of anatomical landmarks), either automatically or with input from a surgeon. The surgery assist computer 102 may further receive subsequent anatomic image information of the patient 10; display a visual representation of the subsequent anatomic image information on the display 108; and may make additional measurements or display additional markers, either automatically or with input from a surgeon.

The surgery assist computer 102 may have a receiver to receive information and data, including image data from the x-ray scanner 16 and/or CT or MR scanner; a processor or microcontroller, such as a CPU, to process the received information and data and to execute other software instructions; system memory to store the received information and data, software instructions, and the like; and a display 108 to display visual representations of received information and data as well as visual representations resulting from other executed system processes.

Figure 2A:
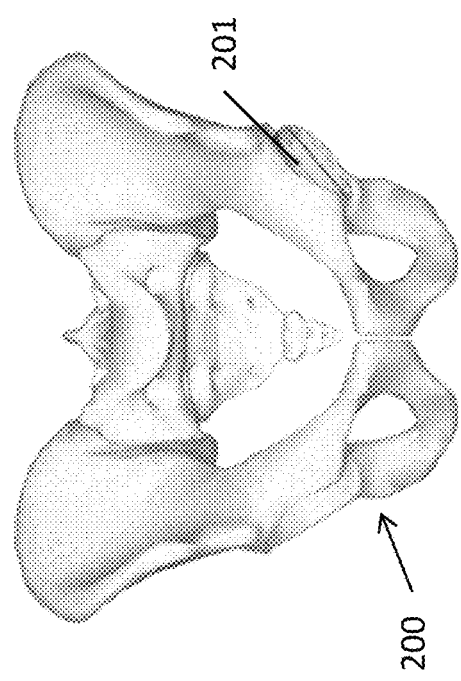
FIG. 2A shows a portion of a patient at a neutral position with no tilt.
Figure 2C:
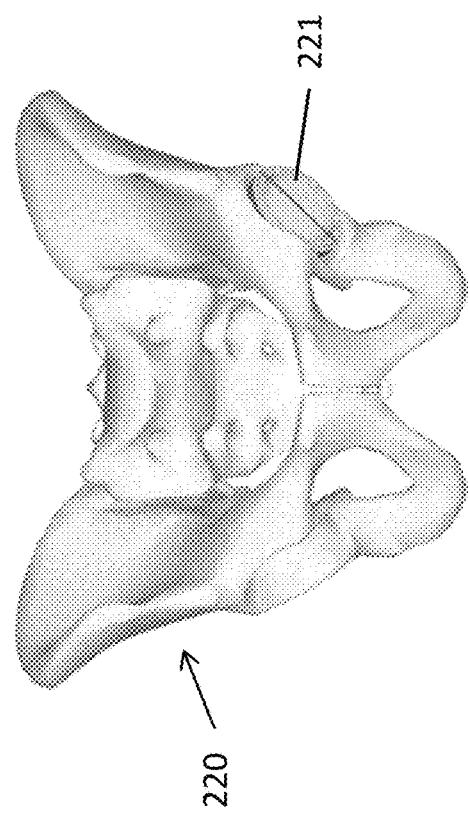
FIG. 2C shows a portion of a patient at a non-neutral position with backward tilt.
Figure 2B:
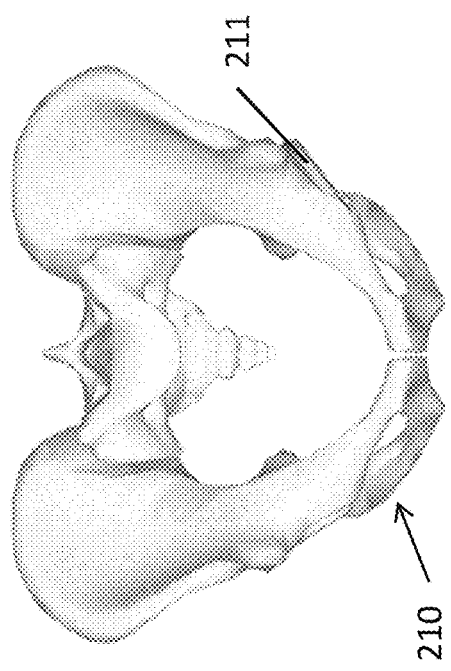
FIG. 2B shows a portion of a patient at a non-neutral position with forward tilt.

Such a system may allow a surgeon and/or other medical personnel to more accurately and consistently determine a proper placement of and position a component by helping a surgeon identify a target position for a component and making adjustments to the positioning value based on differences in initial anatomic image information and subsequent anatomic image information. Such differences may result, for example, when a patient and an imaging scanner are aligned differently with respect to each other when multiple sets of anatomic image information are acquired (e.g., pre-operatively at a neutral position of a patient and intra-operatively at a non-neutral position of the patient). FIGS. 2A-2C provide examples of a portion of a patient 200 (in this case the patient's pelvis) may appear differently when a patient is positioned in different orientations. For example, FIG. 2A shows a portion of the patient 200 in a neutral position with no tilt, while FIG. 2B shows a portion of the patient 210 with a forward tilt of about 20 degrees, and FIG. 2C shows a portion of the patient 220 having a backward tilt of about −20 degrees. Of course, moving a patient may also cause the portion of the patient to have different inclinations and anteversions, as a patient is generally manipulated in three-dimensional space. Importantly, small differences in a patient's orientation relative to a neutral position may provide different measurements of anatomical or component orientations, which could affect the outcome of a surgical procedure. For example, an acetabular cup 201 is positioned with an inclination of 40.0° and an anteversion of 20.0°. If pelvis 200 is tilted 20.0°, as pelvis 210 is in FIG. 2B, the acetabular cup 211 is measured to have an inclination of 37.3° and an anteversion of 4.3°. If pelvis 200 is tilted to −20.0°, as is pelvis 220 in FIG. 2C, the acetabular cup 221 is measured to have an inclination of 47.2° and an anteversion of 34.6°. Accordingly, when positioning a component in a patient during surgery, such as an acetabular cup during THA, a surgeon may need to account for the effects of the patient's orientation on positioning values such as tilt, inclination, and/or anteversion.

Figure 5:
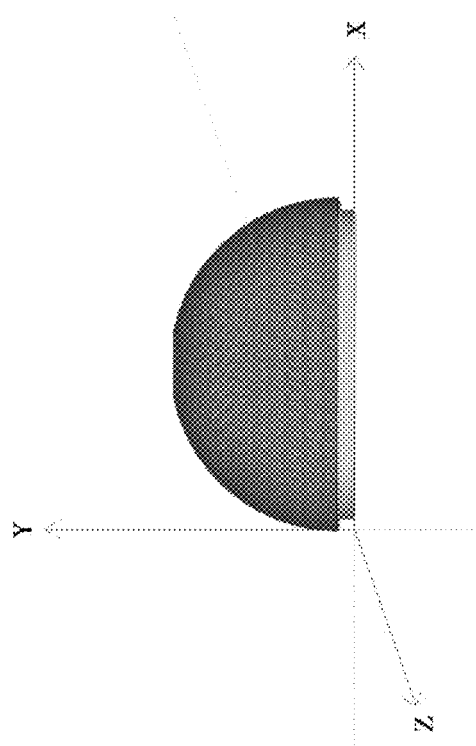
FIG. 5 shows a projected circle rotated along three axes that may be used to model an acetabular cup component in accordance with an embodiment of the present disclosure.

Adjustments to positional values of the acetabular cup, such as inclination, may be based on the study of a projected circle in three-dimensional space. The rotation of the circle in three-dimensional space may mimic the rotation of an acetabular cup. An acetabular cup may display shapes of ellipses under different angles of projection. Three rotational factors may affect the shape of the projected ellipse: Inclination (I)—rotation about the Z axis, Anteversion (A)—rotation about the Y axis, and Tilt (T)—rotation about the X axis. FIG. 5 illustrates an exemplary projection of a circle that may be used to model an acetabular cup with the X, Y, and Z axes labeled.

With reference to FIG. 5, the rotational matrices along the X, Y, and Z axes may be described as follows:

$$R_x(T) = \begin{bmatrix} 1 & 0 & 0 \\ 0 & \cos(T) & -\sin(T) \\ 0 & \sin(T) & \cos(T) \end{bmatrix}$$

$$R_y(A) = \begin{bmatrix} \cos(A) & 0 & \sin(A) \\ 0 & 1 & 0 \\ -\sin(A) & 0 & \cos(A) \end{bmatrix}$$

$$R_z(I) = \begin{bmatrix} \cos(I) & -\sin(I) & 0 \\ \sin(I) & \cos(I) & 0 \\ 0 & 0 & 1 \end{bmatrix}$$

The following matrix may capture the initial circle lying on the X-Z plane:

$$\text{circle} = \begin{bmatrix} R*\sin(\theta) \\ 0 \\ R*\cos(\theta) \end{bmatrix}$$

The normal of the circle may be in the direction of the Y-axis and may be described as follows:

$$\text{Normal} = \begin{bmatrix} 0 \\ -1 \\ 0 \end{bmatrix}$$

After three rotations, the parametric equations of the circle projected on the X-Y plane may be described as follows:

$X = R*[\sin(\theta)*\cos(I)*\cos(A)+\cos(\theta)*\sin(A)]$; and $Y = R*\cos(T)*\sin(\theta)*\sin(I)-R*[-\sin(\theta)*\cos(I)*\sin(A) *\sin(T)+\cos(\theta)*\cos(A)*\sin(T)]$.

where X and Y represent the coordinates of the projected ellipse on the X-Y plane, R represents the size of the acetabular cup, and θ represents the parameter.

After three rotations along the three axes, the parametric equations of the normal of the circle surface may be described as follows:

$X_{normal} = \sin(I)*\cos(A)$ $Y_{normal} = -\cos(I)*\cos(T)+\sin(I)*\sin(A)*\sin(T)$ The normal of the circle has the property that it is always parallel to the minor diameter of the projected ellipse. Accordingly, the minor diameter of the projected ellipse may be derived and described as follows:

Minor Diameter $= \sin(a \cos(\sqrt{X_{normal}^2 + Y_{normal}^2}))*2*R$

The major diameter may be described as follows:

Major Diameter $= 2*R$

Accordingly, the inclination value of the projected ellipse may be described as follows:

$$\text{Projected Ellipse Incl.} = \text{atan}\left(\frac{X_{normal}}{Y_{normal}}\right)$$

Therefore, if an acetabular cup is placed or has target positioning values with a known inclination and anteversion, the inclination resulting after the acetabular cup is tilted (e.g., when the pelvis is tilted) may be calculated. Other positioning values may similarly be calculated, as will be apparent to one of ordinary skill in the art.

Unless otherwise expressly stated or obviously required by context, steps in methods described herein need not be performed in a particular order. Rather, an example order may be provided for ease of explanation.

Figure 3:
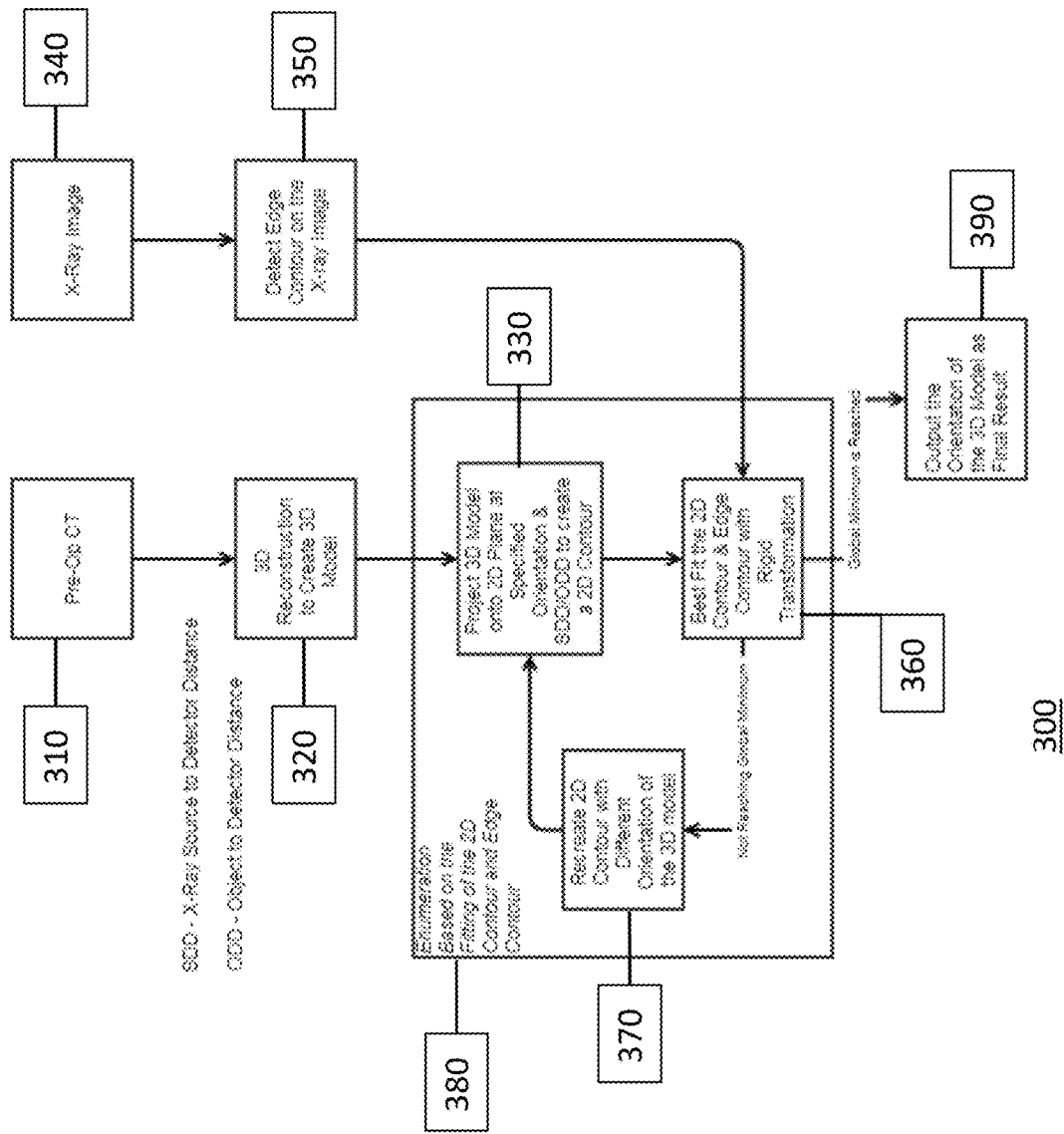
FIG. 3 is an exemplary flow chart diagram illustrating steps that may be taken to render one or more two-dimensional projections from a three-dimensional model of a portion of a patient in accordance with an embodiment of the present disclosure.

In an embodiment, the surgery assist computer 102 may be configured to implement one or more methods of the present disclosure. For example, with reference to FIG. 3, one method 300 may be used to position a component intra-operatively. The example method 300 may include a step 310 of receiving a data set of imaging information representing at least a first portion of a patient (e.g., a data set of three-dimensional imaging information from a CT or MR scan) in a neutral position. Method 300 may further include a step 320 of generating a three-dimensional model of the first portion of the patient based on the data set of imaging information. The three-dimensional model may be reconstructed based on a region grow algorithm, water shed algorithm, active contour algorithm, a combination of algorithms, or any algorithm that may be known to those of ordinary skill in the art for generating a three-dimensional model from a data set of imaging information. Method 300 may additionally include a step 330 of iteratively rendering a plurality of two-dimensional projections from the three-dimensional model, each two-dimensional projection having a corresponding spatial orientation. The two-dimensional projections may be made at a specified orientation and distance (e.g., an x-ray-source-to-detector distance or an object-to-detector distance). Alternatively, method 300 may include a step 330 of rendering a first two-dimensional projection from the three-dimensional model, the first two-dimensional projection having a corresponding spatial orientation, proceeding through step 360 (described in example form below), then repeating step 330 with a next sequential projection (or even an out of order projection).

Method 300 may include a step 340 of receiving intra-operative imaging information (e.g., an intra-operative x-ray image) representing the first portion of the patient. Method 300 may further include a step 350 of identifying a bony edge contour in the intra-operative imaging information. In an embodiment, the bony edge contour in the intra-operative imaging information may be detected using a canny edge detector algorithm, another edge-detection algorithm that may be known to those of ordinary skill in the art, a combination of algorithms, shape-based segmentation, or manual selection. In an embodiment, a canny edge detector process, such as in the exemplary process described above, may include the following steps: (1) apply a Gaussian filter to smooth the image in order to remove noise; (2) find the intensity gradients of the image; (3) apply non-maximum suppression to get rid of spurious responses to edge detection; (4) apply double threshold to determine potential edges; and (5) track by hysteresis to finalize the detection of edges by suppressing all the other edges that are weak and not connected to strong edges.

Method 300 may further include the step 360 of scoring each two-dimensional projection by calculating the distance of the bony edge contour in the intra-operative imaging information to a corresponding contour in each two-dimensional projection and identifying a global minimum score. Scoring step 360 may be performed using best-fit techniques. In an alternate embodiment, such as when the system initially renders only a first two-dimensional projection before proceeding through the method, step 360 may include scoring only the first two-dimensional projection, storing the score in memory, and repeating scoring step 360 for subsequent two-dimensional projections as they are rendered, then selecting a global minimum score from the plurality of scores. A repetitive process such as this may be illustrated by steps 330, 360, and 370 in FIG. 3. The process of repeating 330, 360, and 370 may be referred to as an enumeration process 380 based on the fitting of the two-dimensional projection and the detected bony edge contour from the intra-operative imaging information.

Method 300 may include a step 390 of outputting the orientation of the three-dimensional model as a final result. In an embodiment, step 390 may include outputting a transformation matrix for the two-dimensional projection having the global minimum score, the transformation matrix representing the orientation of the three-dimensional model relative to the neutral position when the two-dimensional projection having the global minimum score was rendered.

Figure 6:
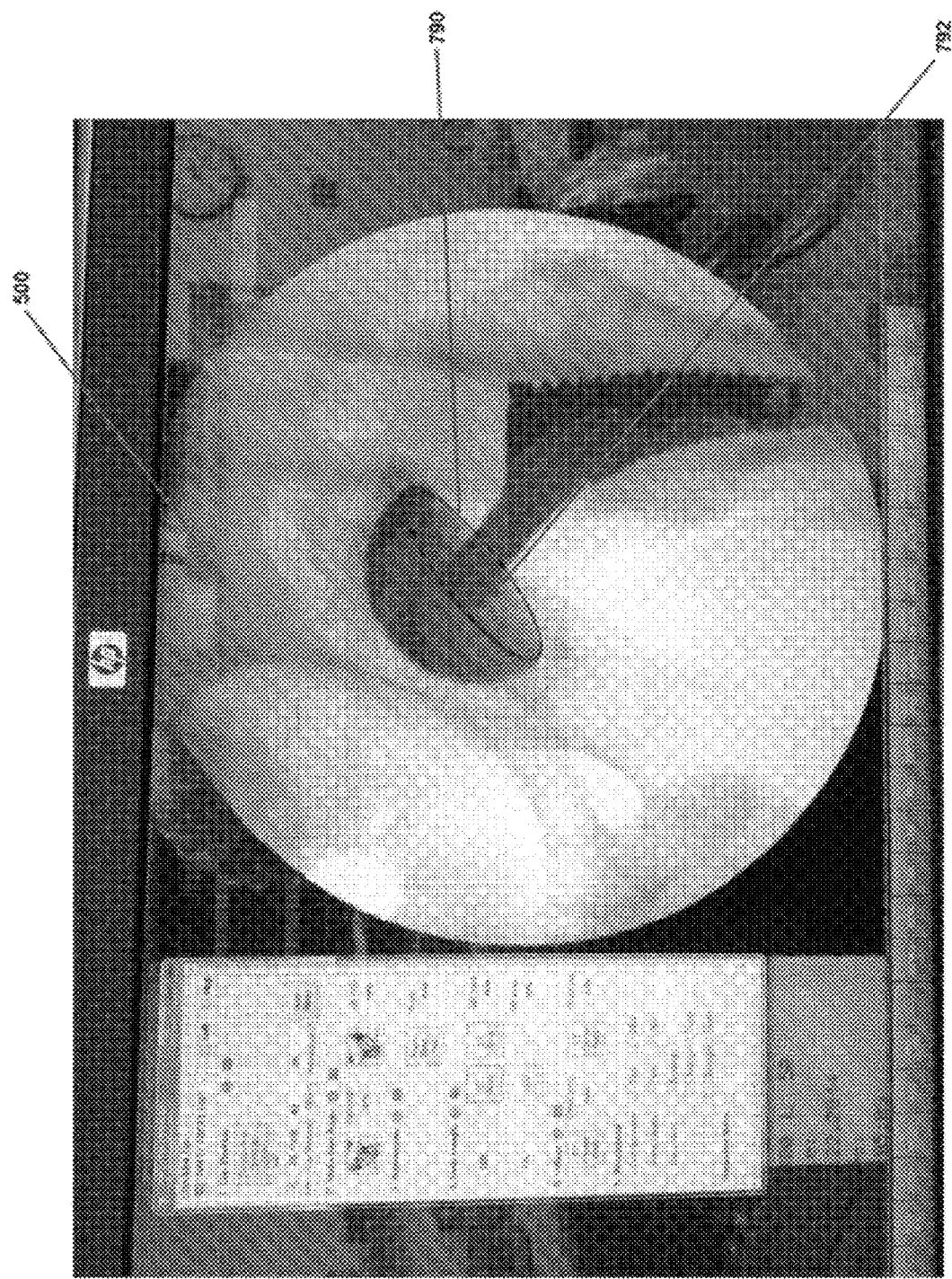
FIG. 6 shows a screen shot of a display including an intra-operative radiographic image including a superimposed ellipse representing a target placement of an acetabular cup component in accordance with an embodiment of the present disclosure.

In an embodiment, a method may include a step of calculating an adjustment factor based on the transformation matrix. The calculated adjustment factor may be used to output a visual indication of an intra-operative adjustment to be made to a component based on the adjustment factor to achieve a target component orientation. For example, FIG. 6 illustrates one embodiment of such a visual indication 790. Still referencing FIG. 6, for example, in a THA surgical procedure, an image of an ellipse 790 may be superimposed onto radiographic image 500 to illustrate how the opening of acetabular cup 792 should appear when properly aligned. In an alternate embodiment, a method may include the step of applying the calculated adjustment factor to an intra-operative leg length measurement and outputting a visual indication of an intra-operative adjustment to be made to the patient to achieve a target leg length measurement. In an embodiment, the radiographic image 500 (and any visual indication discussed in a similar context) may be displayed on display 108 from FIG. 1. In an embodiment, a visual indication may include an outline of the target component orientation; real-time inclination, anteversion, and tilt values of the component; target inclination, anteversion, and tilt values of the component; and/or combinations thereof.

Figure 4:
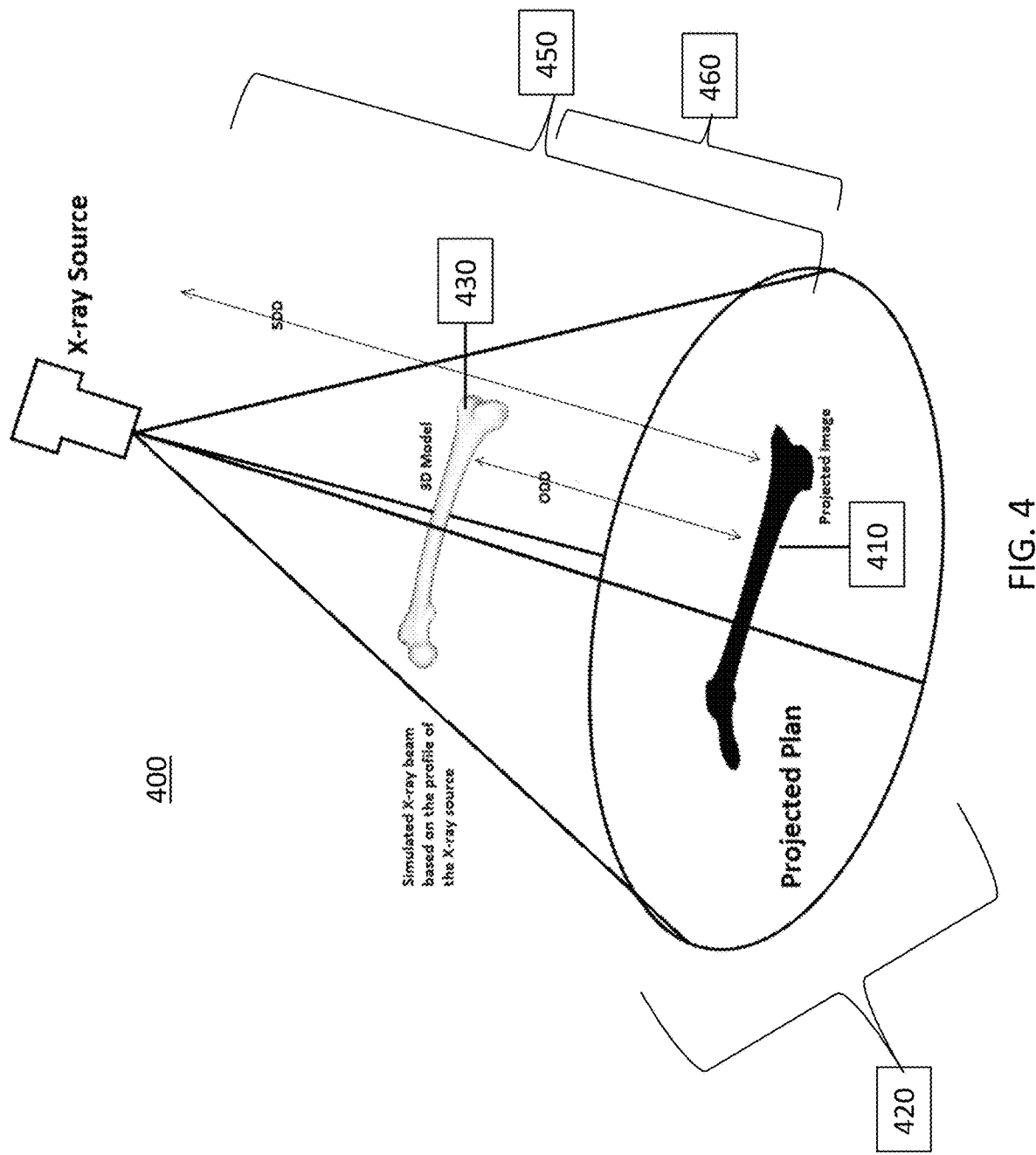
FIG. 4 is a diagram providing a conceptual model of a two-dimensional projection from a three-dimensional model in accordance with an embodiment of the present disclosure.

FIG. 4 illustrates a conceptual model of a two-dimensional projection from a three-dimensional model 400 in accordance with an embodiment of the present disclosure. As discussed above, one or more two-dimensional projection(s) 410 may be rendered based on the three-dimensional model 430 onto a projected plan view 420. Projected plan view 420 may be comparable to an x-ray image, where the two-dimensional projection 410 may be comparable to an anatomical visualization on an x-ray image. Each two-dimensional projection may have a corresponding spatial orientation depending on the position of the x-ray source 16a to the three-dimensional model 430. Of course, FIG. 4 may represent a conceptualization of rendering two-dimensional projections, so there is not necessarily a physical x-ray source 16a or a physical three-dimensional model 430 (though it may be possible to visualize the three-dimensional model 430 on the display 108 in some embodiments). The two-dimensional projections may be rendered at a specified orientation and distance (e.g., an x-ray-source-to-detector distance 440 or an object-to-detector distance 450). The spatial relationship of the x-ray source 16a and the three-dimensional model 430 as well as distance(s) 450, 460 may want to be taken into account in certain embodiments to ensure accurate measurements.

In an embodiment, systems and methods of the present disclosure may be used to ensure consistent measurements between radiographic images taken of a patient at a neutral position and radiographic images taken of a patient in a non-neutral (e.g., intra-operative) position without having to ensure that the patient is precisely placed in a neutral position and, potentially, with less x-ray exposure, by simulating movement of the patient back to the neutral position using the three-dimensional model and calculating an adjustment factor taking into account the differences between the actual, non-neutral position of the patient and the patient in a neutral position.

Figure 7:
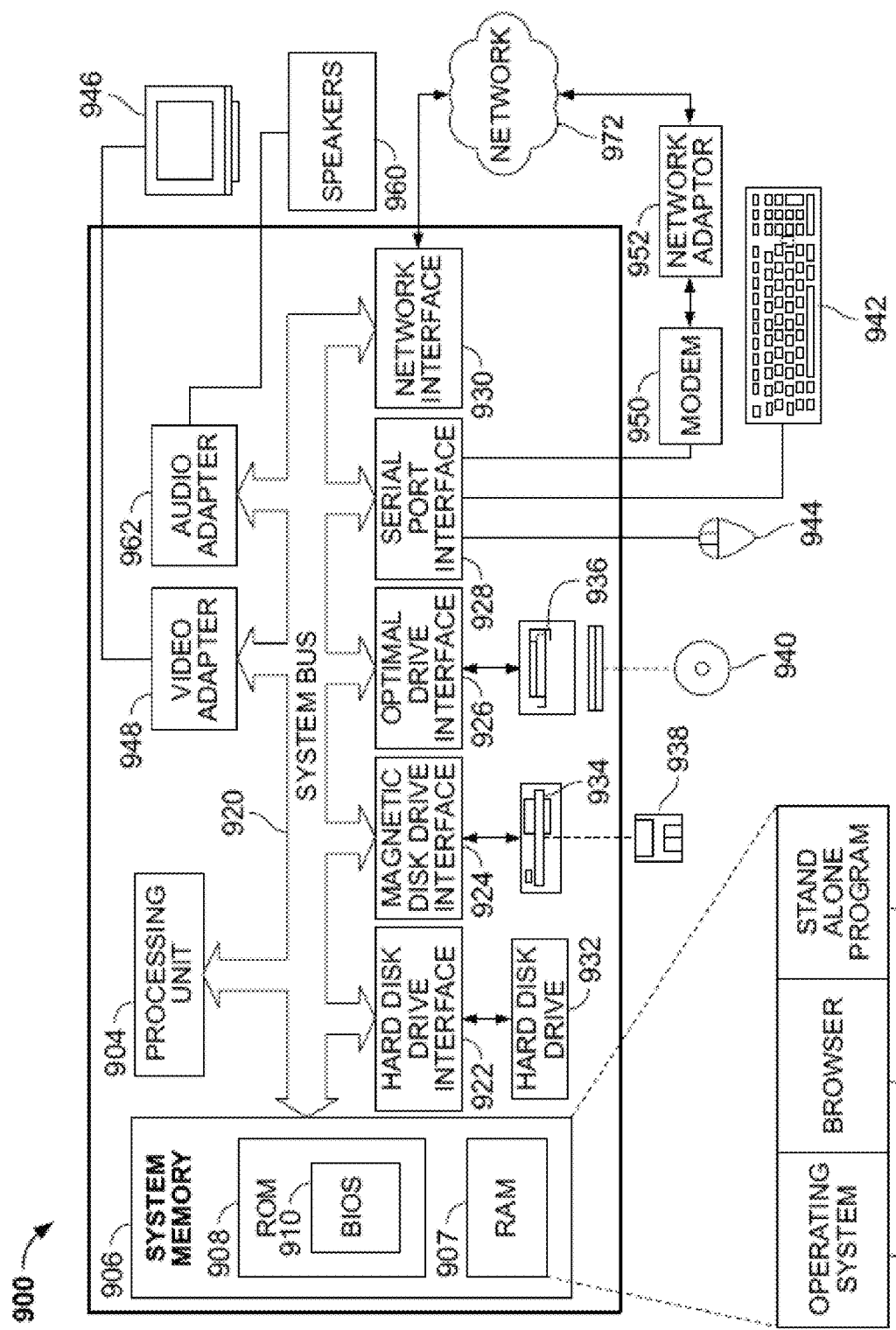
FIG. 7 shows an embodiment of a computer architecture according to the present disclosure.

FIG. 7 depicts exemplary hardware for a system to generate and utilize a three-dimensional patient model to determine a proper placement of a component during a surgery. The system, or part thereof, may take the form of a computer 900 that includes a processing unit 904, a system memory 906, and a system bus 920 that operatively couples various system components, including the system memory 906 to the processing unit 904. There may be only one or there may be more than one processing unit 904, such that the processor of computer 900 comprises a single central processing unit (CPU), or a plurality of processing units, commonly referred to as a parallel processing environment. The computer 900 may be a conventional computer, a distributed computer, a web server, a file server, a tablet or iPad, a smart phone, or any other type of computing device.

The system bus 920 may be any of several types of bus structures including a memory bus or memory controller, a peripheral bus, a switched fabric, point-to-point connections, and a local bus using any of a variety of bus architectures. The system memory 906 may also be referred to as simply the memory, and includes read only memory (ROM) 908 and random access memory (RAM) 907. A basic input/output system (BIOS) 910, containing the basic routines that help to transfer information between elements within the computer 900, such as during start-up, is stored in ROM 908. The computer 900 may further include a hard disk drive 932 for reading from and writing to a hard disk, not shown, a magnetic disk drive 934 for reading from or writing to a removable magnetic disk 938, and/or an optical disk drive 936 for reading from or writing to a removable optical disk 940 such as a CD-ROM or other optical media.

The hard disk drive 932, magnetic disk drive 934, and optical disk drive 936 may be connected to the system bus 920 by a hard disk drive interface 922, a magnetic disk drive interface 924, and an optical disk drive interface 926, respectively. The drives and their associated computer-readable media provide nonvolatile storage of computer-readable instructions; data structures, e.g., a catalog and a context-based index; program modules, e.g., a web service and an indexing robot; and other data for the computer 900. It should be appreciated by those skilled in the art that any type of computer-readable media that can store data that is accessible by a computer, for example, magnetic cassettes, flash memory cards, USB drives, digital video disks, RAM, and ROM, may be used in the exemplary operating environment.

A number of program modules may be stored on the hard disk 932, magnetic disk 934, optical disk 936, ROM 908, or RAM 907, including an operating system 912, browser 914, stand alone program 916, etc. A user may enter commands and information into the personal computer 900 through input devices such as a keyboard 942 and a pointing device 944, for example, a mouse. Other input devices (not shown) may include, for example, a microphone, a joystick, a game pad, a tablet, a touch screen device, a satellite dish, a scanner, a facsimile machine, and a video camera. These and other input devices are often connected to the processing unit 904 through a serial port interface 928 that is coupled to the system bus 920, but may be connected by other interfaces, such as a parallel port, game port or a universal serial bus (USB).

A monitor 946 or other type of display device is also connected to the system bus 920 via an interface, such as a video adapter 948. In addition to the monitor 946, computers typically include other peripheral output devices, such as speakers 960 connected to the system bus 920 via an audio adapter 962, and printers. These and other output devices are often connected to the processing unit 904 through the serial port interface 928 that is coupled to the system bus 920, but may be connected by other interfaces, such as a parallel port, game port, or a universal serial bus (USB).

The computer 900 may operate in a networked environment using logical connections to one or more remote computers. These logical connections may be achieved by a communication device coupled to or integral with the computer 900; the application is not limited to a particular type of communications device. The remote computer may be another computer, a server, a router, a network personal computer, a client, a peer device, or other common network node, and typically includes many or all of the elements described above relative to the computer 900, although only a memory storage device has been illustrated in FIG. 9. The computer 900 can be logically connected to the Internet 972. The logical connection can include a local area network (LAN), wide area network (WAN), personal area network (PAN), campus area network (CAN), metropolitan area network (MAN), or global area network (GAN). Such networking environments are commonplace in office networks, enterprise-wide computer networks, intranets and the Internet, which are all types of networks.

When used in a LAN environment, the computer 900 may be connected to the local network through a network interface or adapter 930, which is one type of communications device. When used in a WAN environment, the computer 900 typically includes a modem 950, a network adapter 952, or any other type of communications device for establishing communications over the wide area network. The modem 950, which may be internal or external, is connected to the system bus 920 via the serial port interface 928. In a networked environment, program modules depicted relative to the personal computer 900, or portions thereof, may be stored in a remote memory storage device. It is appreciated that the network connections shown are exemplary and other means of, and communications devices for, establishing a communications link between the computers may be used.

The system can take the form of a computer program product 916 accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

The medium can be an apparatus or device that utilizes or implements electronic, magnetic, optical, electromagnetic, infrared signal or other propagation medium, or semiconductor system. Examples of a computer-readable medium comprise a semiconductor or solid-state memory, magnetic tape, a removable computer diskette, a random access memory, a read-only memory, a rigid magnetic disk and an optical disk. Current examples of optical disks comprise compact disk-read only memory (CD-ROM), compact disk-read/write (CD-R/W) and DVD formats.

A data processing system suitable for storing and/or executing program code comprises at least one processor coupled directly or indirectly to memory elements through a system bus. The memory elements can include local memory employed during actual execution of the program code, bulk storage, and cache memory that provide temporary storage of at least some program code in order to reduce the number of times code is retrieved from bulk storage during execution.

Input/output or I/O devices (including, but not limited to, keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modems and Ethernet cards are just a few of the currently available types of network adapters.

Furthermore, computers and other related electronic devices can be remotely connected to either the LANs or the WAN via a digital communications device, modem and temporary telephone, or a wireless link. It will be appreciated that the Internet comprises a vast number of such interconnected networks, computers, and routers.

Figure 8:
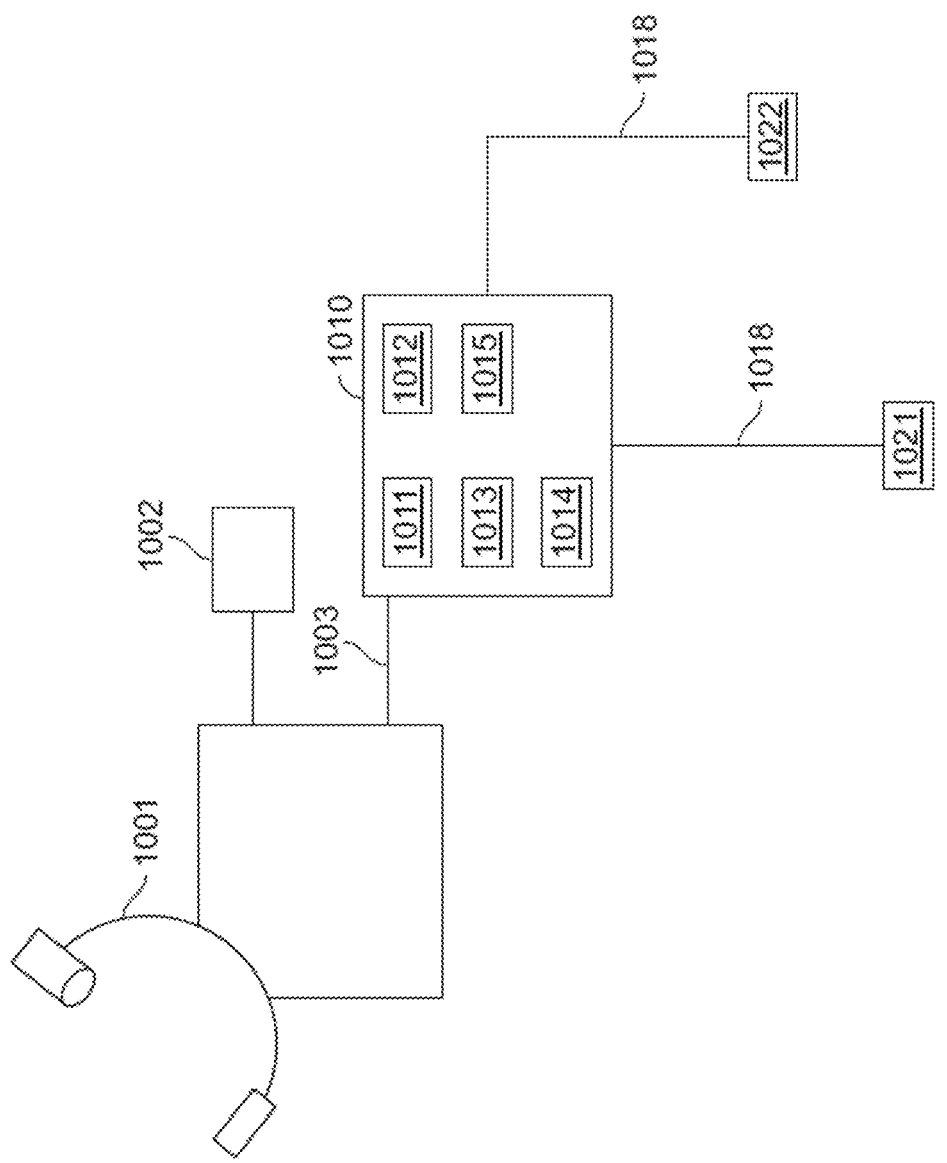
FIG. 8 depicts a block diagram of an exemplary environment that may be used to implement at least parts of the systems and methods of the present disclosure.

The methods and systems described in the present disclosure may be implemented, at least in part, using certain hardware. For example, referring to FIG. 8, a C-arm apparatus 1001 may capture video or image signals using x-rays. C-arm apparatus 1001 may, for example, capture an intra-operative x-ray image. The C-arm apparatus 1001 may have a display 1002 directly connected to the apparatus to instantly view the images or video. Display 1002 may be configured with a number of various inputs, including, for example, an input to receive one or more data sets of three-dimensional image information. A wireless kit 1010 may, alternatively or additionally, be attached to the C-arm apparatus 1001 via video port 1003 to receive the video or image signal from the C-arm apparatus 1001, the signal representing digital data of a radiographic image frame or plurality of frames. Video port 1003 may utilize a BNC connection, a VGA connection, a DVI-D connection, or an alternative connection known to those of skill in the art. Unique in the field in its ability to convert any wired image acquisition device (such as a C-arm) into a wireless imaging device, the wireless kit 1010 may be the Radlink Wireless C-Arm Kit. Wireless kit 1010 may include a resolution converter 1011 to convert the image signal to proper resolution for further transmission, frame grabber 1012 to produce a pixel-by-pixel digital copy of each image frame, central processing unit 1013, memory 1014, and dual-band wireless-N adapter 1015. The wireless kit 1010 may convert the received signal to one or more image files and can send the converted file(s), for example, by wireless connection 1018 to one or more computer(s) and operatively connected display(s) 1021, 1022. The computer and operatively connected display may, for example, be a Radlink Galileo Positioning System ("GPS") 1021 or GPS Tablet 1022. The Wireless C-Arm Kit 1010 may receive, convert, and transmit the file(s) in real time. The methods described in the present disclosure may be implemented, for example, as software running on the GPS 1021 or GPS Tablet 1022 units. The GPS 1021 and GPS Tablet 1022 may also incorporate additional functions, such as those provided in the Radlink Pro Imaging with Surgeon's Checklist software.

While various aspects and embodiments have been disclosed herein, other aspects and embodiments will be apparent to those skilled in the art. The various aspects and embodiments disclosed herein are for purposes of illustration and are not intended to be limiting.

What is claimed is:

1. A method of positioning a component intra-operatively comprising the steps of:

iteratively registering a plurality of two-dimensional projections of a portion of a patient from a three-dimensional model of the portion of the patient, the three-dimensional model being generated from a data set of imaging information obtained at a neutral position, and each two-dimensional projection having a spatial orientation;

scoring each two-dimensional projection against an intra-operative image by determining a best fit of each projection to the intra-operative image and calculating a spatial difference between corresponding points;

identifying a global minimum score reflecting the smallest spatial difference between the corresponding points on the two-dimensional projection and the intra-operative image and selecting the two-dimensional projection having the global minimum score as an intra-operative projection;

obtaining values representing the orientation of the three-dimensional model corresponding to the intra-operative projection; and calculating an adjustment factor based on the difference in the values representing the orientation of the three-dimensional model at the intra-operative projection position and values representing the orientation of the three-dimensional model at the neutral position.

2. The method of claim 1, further comprising the step of outputting a visual indication of an intra-operative adjustment to be made to a component based on the adjustment factor to achieve a target component orientation.

3. The method of claim 1, further comprising the step of applying the adjustment factor to an intra-operative leg length measurement and outputting a visual indication of an intra-operative adjustment to be made to the patient to achieve a target leg length measurement.

4. The method of claim 2, wherein the component is one of an acetabular cup and a femoral prosthesis.

5. The method of claim 1, wherein the step of scoring a first two-dimensional projection occurs before or during the step of registering a subsequent two-dimensional projection.

6. The method of claim 1, wherein each of the plurality of two-dimensional projections is registered before scoring any two-dimensional projection.

7. The method of claim 1, further comprising identifying a reference point on the intra-operative image using one of a canny edge detector algorithm, a shape-based segmentation algorithm, manual selection, and a combination thereof.

8. The method of claim 1, wherein the three-dimensional model of the portion of the patient is generated by applying one of a region grow algorithm, a water shed algorithm, an active contour algorithm, and a combination thereof to the data set of imaging information.

9. A method for positioning a component intra-operatively comprising the steps of:

receiving a data set of imaging information representing at least a first portion of a patient in a neutral position;

generating a three-dimensional model of the first portion of the patient based on the data set of imaging information;

receiving intra-operative imaging information representing the first portion of the patient; identifying a bony edge contour in the intra-operative imaging information;

iteratively rendering a plurality of two-dimensional projections from the three-dimensional model, each two-dimensional projection having a corresponding spatial orientation;

scoring each two-dimensional projection against the intra-operative imaging information by determining a best fit of each projection to the intra-operative image and calculating the distance of the bony edge contour in the intra-operative imaging information to a corresponding contour in each two-dimensional projection and identifying a global minimum score reflecting the smallest spatial difference between the corresponding points on the two-dimensional projection and the intra-operative image;

selecting the two-dimensional projection having the global minimum score as an intra-operative projection;

outputting a transformation matrix for the two-dimensional projection having the global minimum score, the transformation matrix representing the orientation of the three-dimensional model relative to the neutral position when the two-dimensional projection having the global minimum score was rendered; and calculating an adjustment factor based on the transformation matrix.

10. The method of claim 9, further comprising the step of outputting a visual indication of an intra-operative adjustment to be made to a component based on the adjustment factor to achieve a target component orientation.

11. The method of claim 10, wherein the component is one of an acetabular cup and a femoral prosthesis.

12. The method of claim 9, further comprising the step of applying the adjustment factor to an intra-operative leg length measurement and outputting a visual indication of an intra-operative adjustment to be made to the patient to achieve a target leg length measurement.

13. The method of claim 9, wherein the step of scoring a first two-dimensional projection occurs before or during the rendering of one or more subsequent two-dimensional projections.

14. The method of claim 9, wherein each of the plurality of two-dimensional projections is rendered before scoring any two-dimensional projection.

15. The method of claim 9, wherein the bony edge contour of the intra-operative imaging information is identified using one of a canny edge detector algorithm, a shape-based segmentation algorithm, manual selection, and a combination thereof.

16. The method of claim 9, wherein the three-dimensional model of the first portion of the patient is generated by applying one of a region grow algorithm, a water shed algorithm, an active contour algorithm, and a combination thereof to the data set of imaging information.

17. An imaging system for intra-operatively positioning a component, comprising:

a computerized display system including a display, a receiver, and a microcontroller operatively coupled to the display and to the receiver and having access to system memory, the system memory including software instruction causing the microcontroller to perform the steps of:

receiving a data set of imaging information representing at least a first portion of a patient in a neutral position;

generating a three-dimensional model of the first portion of the patient based on the data set of imaging information;

receiving intra-operative imaging information representing the first portion of the patient;

identifying a bony edge contour in the intra-operative imaging information;

iteratively rendering a plurality of two-dimensional projections from the three-dimensional model, each two-dimensional projection having a corresponding spatial orientation;

scoring each two-dimensional projection against the intra-operative imaging information by determining a best fit of each projection to the intra-operative image and calculating the distance of the bony edge contour in the intra-operative imaging information to a corresponding contour in each two-dimensional projection and identifying a global minimum score reflecting the smallest spatial difference between the corresponding points on the two-dimensional projection and the intra-operative image;

selecting the two-dimensional projection having the global minimum score as an intra-operative projection;

outputting a transformation matrix for the two-dimensional projection having the global minimum score, the transformation matrix representing the orientation of the three-dimensional model relative to the neutral position when the two-dimensional projection having the global minimum score was rendered;

calculating an adjustment factor based on the transformation matrix; and outputting to the display a visual indication of an intra-operative adjustment to be made to a component based on the adjustment factor to achieve a target component orientation.

18. The system of claim 17, wherein the component is one of an acetabular cup and a femoral prosthesis.

19. The system of claim 17, wherein:
the component is an acetabular cup; and
the visual indication comprises at least one of an outline of the target component orientation; real-time inclination, anteversion, and tilt values of the component; target inclination, anteversion, and tilt values of the component; and combinations thereof.

20. The system of claim 17, wherein the bony edge contour of the intra-operative imaging information is identified using one of a canny edge detector algorithm, a shape-based segmentation algorithm, manual selection, and a combination thereof.

21. A method for intra-operatively positioning a component comprising the steps of:
receiving a data set of imaging information representing a portion of a patient in a neutral position and generating a three-dimensional model of the portion of the patient from the data set;
receiving an intra-operative image of the portion of the patient;
rendering a plurality of two-dimensional projections from the three-dimensional model;
scoring each two-dimensional projection against the intra-operative image by determining a best fit of each projection to the intra-operative image and calculating a spatial difference between corresponding points;
identifying a global minimum score reflecting the smallest spatial difference between the corresponding points on the two-dimensional projection and the intra-operative image;
selecting the two-dimensional projection having the global minimum score as an intra-operative projection; and
calculating an adjustment factor by comparing a difference in orientation of the three-dimensional model at a neutral position and the three-dimensional model at the orientation corresponding to the best-fit two-dimensional projection.

* * * * *